(12) United States Patent
Harada

(10) Patent No.: US 8,709,041 B2
(45) Date of Patent: Apr. 29, 2014

(54) CHIROPRACTIC APPARATUS CAPABLE OF FORMING A RELEASE SURFACE

(76) Inventor: Masanori Harada, Fukuoka (JP)

( * ) Notice: Subject to any disclaimer, the term of this patent is extended or adjusted under 35 U.S.C. 154(b) by 0 days.

(21) Appl. No.: 13/818,156

(22) PCT Filed: Oct. 23, 2010

(86) PCT No.: PCT/JP2010/068680
§ 371 (c)(1),
(2), (4) Date: Feb. 21, 2013

(87) PCT Pub. No.: WO2012/032677
PCT Pub. Date: Mar. 15, 2012

(65) Prior Publication Data
US 2013/0158602 A1    Jun. 20, 2013

(30) Foreign Application Priority Data
Sep. 9, 2010  (JP) ................................. 2010-201575

(51) Int. Cl.
*A61H 23/00*    (2006.01)
*A61F 5/00*    (2006.01)

(52) U.S. Cl.
USPC ............. 606/239; 601/84; 601/107; 606/237; 606/238

(58) Field of Classification Search
USPC .......... 606/237–239; 601/46, 84, 97–98, 101, 601/107–108, 103, 110, 111, 78–81
See application file for complete search history.

(56) References Cited

U.S. PATENT DOCUMENTS

| | | | | |
|---|---|---|---|---|
| 3,396,721 A | * | 8/1968 | Mencacci | 601/107 |
| 5,356,369 A | * | 10/1994 | Yamasaki et al. | 601/70 |
| 5,361,437 A | * | 11/1994 | Zhu et al. | 5/639 |
| 5,645,522 A | * | 7/1997 | Lurie et al. | 601/43 |
| 5,785,668 A | * | 7/1998 | Shimizu | 601/50 |
| 6,146,342 A | * | 11/2000 | Glen | 601/61 |

(Continued)

FOREIGN PATENT DOCUMENTS

| | | |
|---|---|---|
| EP | 2161010 A1 | 10/2010 |
| JP | 2009-005892 | 1/2009 |
| JP | 0004523998 | 8/2010 |

OTHER PUBLICATIONS

International Search Report with Translation issued in connection with PCT/JP2010/068680, Dated: Nov. 30, 2010, pp. 1-7.

*Primary Examiner* — Tatyana Zalukaeva
*Assistant Examiner* — Christopher Miller
(74) *Attorney, Agent, or Firm* — Sutherland Asbill & Brennan LLP

(57) ABSTRACT

A chiropractic apparatus that is not only easily portable, but also enables even a chiropractor not having a high level skill to perform easily a safe, correct and effect adjustment of any bone of a patient without causing a pain. The chiropractic apparatus includes: a chiropractic adjuster containing a thrust member having a thrust head and a release-surface former attached to the chiropractic adjuster, the release-surface former having a preload surface for forming a release surface. When a longitudinal forward thrust is applied to the thrust member so as to give a thrust to a body surface, the release-surface former and the thrust head are subjected to relative movement with respect to each other, whereby a release surface is formed around the thrust head, the release surface having at least a part thereof placed in contact with the body surface.

10 Claims, 13 Drawing Sheets

(56) References Cited

U.S. PATENT DOCUMENTS

| | | | |
|---|---|---|---|
| 6,228,042 B1 * | 5/2001 | Dungan | 601/107 |
| 6,379,375 B1 | 4/2002 | Fuhr | |
| 6,602,211 B2 | 8/2003 | Tucek | |
| 6,805,700 B2 | 10/2004 | Miller | |
| 7,927,259 B1 * | 4/2011 | Rix | 482/83 |
| 2002/0077664 A1 | 6/2002 | Fuhr | |
| 2002/0082532 A1 | 6/2002 | Tucek et al. | |
| 2003/0014079 A1 | 1/2003 | Tucek | |
| 2007/0150004 A1 * | 6/2007 | Colloca et al. | 606/238 |
| 2009/0270915 A1 * | 10/2009 | Tsai et al. | 606/238 |

* cited by examiner

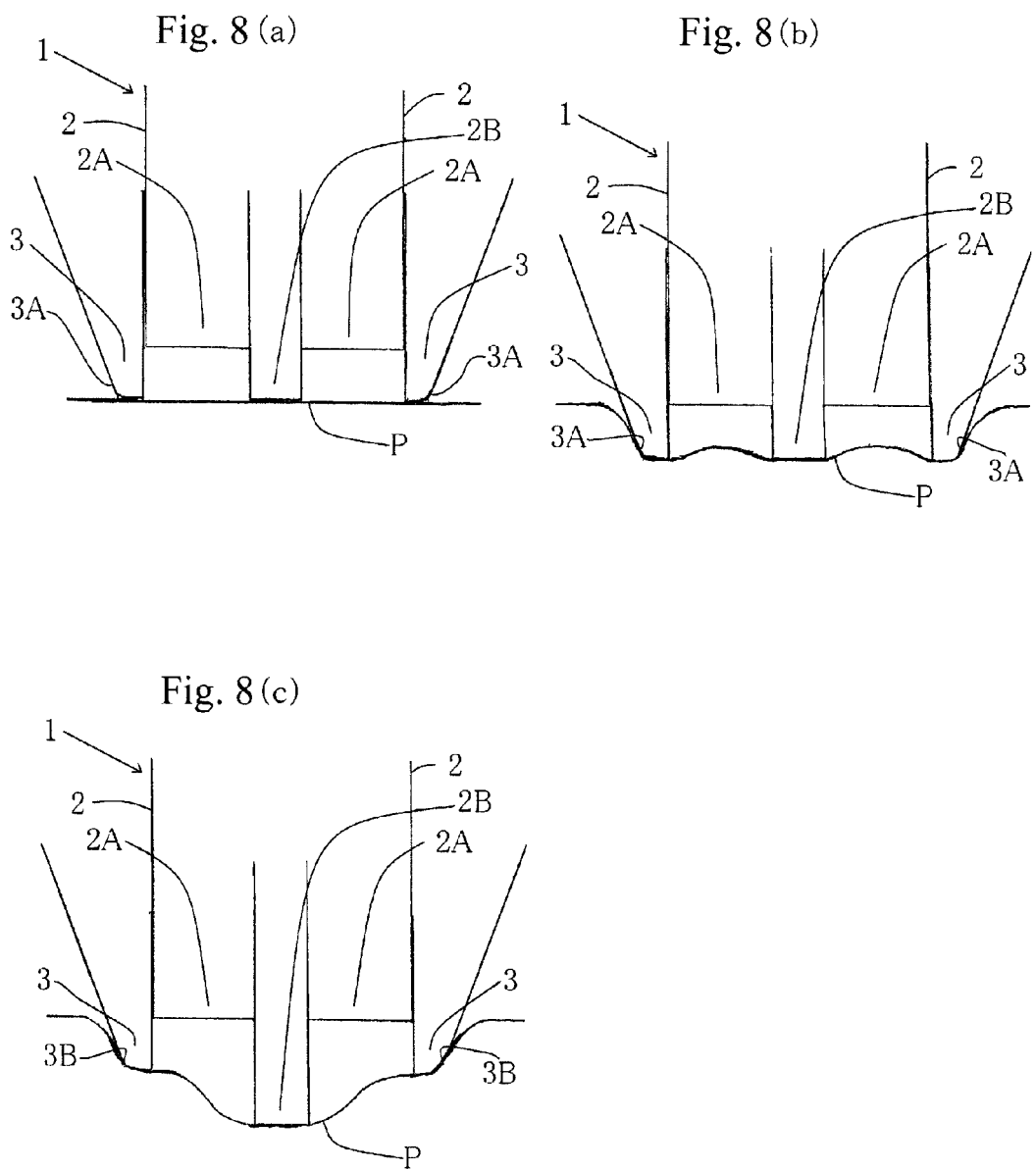

CHIROPRACTIC APPARATUS CAPABLE OF FORMING A RELEASE SURFACE

FIELD OF THE INVENTION

The present invention relates to a chiropractic apparatus capable of forming a release surface. More particularly, the present invention is concerned with a chiropractic apparatus comprising the following means (i) and (ii): (i) a chiropractic adjuster means containing a thrust member having a thrust head, and (ii) a release-surface means attached to the chiropractic adjuster means, the release-surface means having a surface for forming a release surface, wherein, when a longitudinal forward thrust is applied to the thrust member so as to give a thrust to a body surface of a patient, the release-surface means and the thrust head are subjected to relative movement with respect to each other, whereby a release surface comprising the surface for forming a release surface is formed around the thrust head, the release surface having at least a part thereof placed in contact with the body surface of the patient.

By the use of the chiropractic apparatus of the present invention capable of forming a release surface, it becomes possible that, after a target site for chiropractic treatment is determined by performing a palpation on a patient, a satisfactory force of preload can be applied to the body surface of the patient through a relatively large contact area which is the total surface area of the forward end portion (thrust head) of the chiropractic adjuster means and, present therearound, the surface for forming a release surface. Therefore, by virtue of the relatively large contact area, there can be obtained advantages not only in that, during the preload, the patient's pain is small and the chiropractic adjuster means can be stably positioned on the body surface of the patient without causing damage to the body surface tissue, but also in that, after the preload, a satisfactory effect of treatment (adjustment) can be achieved even when using a small force of adjustment. Further, by virtue of the formation of a release surface around the thrust head of the chiropractic adjuster means when performing an adjustment, there can be achieved advantages not only in that the thrust head of the chiropractic adjuster means can be guided to a deep region (near to a target bone for adjustment) in the body of the patient, but also in that a thrust can be correctly applied to a small-area target site in the target bone. Thus, by the use of the chiropractic apparatus of the present invention, chiropractic treatment can be performed more safely, effectively and efficiently. Also, the chiropractic apparatus of the present invention is easily portable.

BACKGROUND OF THE INVENTION

The term "chiropractic" means "hand action" and is a combination of Greek words "Chiro" ("hand") and "Prakticos" ("action"). As indicated by its name, in the field of chiropractic, palpation using various parts of the hands, such as a fingertip and the pisiform bone, is performed on the body of a patient for determining a target site for chiropractic treatment, and then chiropractic treatment is performed by a method in which a thrust (i.e., an impact of high speed and low amplitude) is applied to the target site by using various parts of the hands or by using an apparatus employing spring resilience or electromagnetic force. In the field of chiropractic, amelioration of various diseases and ailments is achieved by applying an appropriate thrust to the cranium, the spine, the lumbar vertebrae, the pelvis, and/or joints of limbs so as to correct small dislocation of these bones. (In the field of chiropractic, such small dislocation of bones is called "subluxation" or "misalignment".) When a portion, to be given a thrust, of the body surface of the patient has a skin slack, the thrust applied is disadvantageously absorbed by the skin slack, thus making it impossible to transmit a satisfactory level of force of thrust to the target site; therefore, generally, before the application of a thrust to the body surface of the patient, the skin of the portion, to be given a thrust, of the body surface of the patient is pulled so as to be placed under tension to remove any skin slack. Also, when a target site for chiropractic treatment is present under a thick layer of fat or muscle, it is a general practice that, in addition to pulling and tensioning the skin of the body surface of the patient to remove a skin slack, a preload is applied to the body surface and the subcutaneous tissue by a method in which either a portion (to be used for applying a thrust) of a hand of the chiropractic practitioner or a forward end portion of a chiropractic apparatus is rather strongly pressed onto the body surface of the patient in the depthwise direction of the body of the patient, thereby increasing the body tissues' ability to allow the propagation of a thrust therethrough. By applying a satisfactory force of preload to the body surface and the subcutaneous tissue of the patient to thereby increase the body tissues' ability to allow the propagation of a thrust therethrough, a chiropractic treatment can be performed even using a relatively small force of adjustment.

In the field of chiropractic, the term "thrust" covers any type of mechanical pressures. As a method for applying a mechanical pressure, there can be mentioned a method in which a fingertip of a chiropractic practitioner or a forward end of a rod (made of a plastic or metal) is placed on the body surface of a patient, and then the fingertip or rod is macroscopically moved to apply a pressure (thrust) to the body surface of the patient. This method is employed in the case where a thrust is applied by using the body of a chiropractic practitioner or the case where a thrust is applied by using a so-called "activator" described below. As another method for applying a mechanical pressure, there can be mentioned a method in which a forward end of a rod (made of a plastic or metal) is placed on the body surface of a patient, and then a mechanical impulse is applied to a rear end of the rod (which is not macroscopically moved) thereby generating a thrust in the form of a pressure wave propagating from the rear end to forward end of the rod to thereby apply a pressure (thrust) to the body surface of the patient. In general, this method is employed only in the case where there is used an apparatus for performing a so-called "Atlas Orthogonal Technique" described below.

In the field of chiropractic, chiropractic treatment (application of a thrust) is usually called "adjustment". Therefore, hereinafter, application of a thrust is frequently referred to as "adjustment". (In the field of chiropractic, the term "manipulation" may be used as having the same meaning as "adjustment".) In the field of chiropractic, a portion, to be given a thrust, of the body surface of the patient is usually referred to as a "contact point". Therefore, hereinafter, a portion, to be given a thrust, of the body surface of the patient is frequently referred to as a "contact point". With respect to the general information of chiropractic and to the above-mentioned various terms, reference can be made to, for example, Non-Patent Document 1 ("Kairopurakutikku-Gairon (Outline of Chiropractic)", authored by Seikyo SUZUKI, published by Taniguchi Shoten Publishing Co., Japan, 1987), Non-Patent Document 2 ("Hajimete Manabu Kairopurakutikku-Sukiru-Kihon-Gensoku-Kara Manipyureishon-Sukiru-Made— (Introduction to Chiropractic Skills—from basic principles to manipulation skills)", authored and edited by David Byfield, translation supervised by Motoaki OTANI, published by IDO-NO-NIPPON SHA INC., Japan, 1999), and Non-Patent Document 3 ("Okai-DC-No Tekunikku-Bukku, Kihon-Hen, Jissen-Kairopurakutikku-Ajasutomento-Tekunikku (Technique Book of Okai DC (Basics) Practical Chiropractic Adjustment Techniques)", authored by Takeshi OKAI, published by Japan Medical Publishing Co. LTD., Japan, 2004). With respect especially to the term "adjustment", reference is made to Non-Patent Documents 1 and 3.

When an adjustment is performed using a finger, such as an index finger or middle finger, problems may arise not only in that a burden is imposed on the finger and the wrist of the chiropractic practitioner (chiropractor), thus causing the chiropractor to suffer injuries, but also in that the direction of the thrust is not correct, thus making it impossible to obtain a desired effect on the patient. When it is necessary to apply a high force thrust, the pisiform bone is used in many cases. However, the pisiform bone is less sensitive as compared to a fingertip, and therefore, a high level skill is required to perform a correct adjustment by using the pisiform bone.

For solving these problems accompanying adjustments performed using the human power, adjustments may be performed using equipment (chiropractic apparatuses). In the case of the use of chiropractic apparatuses, a thrust is applied to the patient by using spring resilience or electromagnetic force. Conventional chiropractic apparatuses are described in, for example, U.S. Patent Application Publication No. US 2002/0082532 A1 (Patent Document 1), U.S. Pat. No. 6,379,375 (Patent Document 2), U.S. Pat. No. 6,602,211 (Patent Document 3), U.S. Pat. No. 6,805,700 (Patent Document 4), and Unexamined Japanese Patent Application Laid-Open Specification No. 2009-5892 (Patent Document 5). These chiropractic apparatuses are generally referred to as "activators", and the chiropractic techniques performed using such chiropractic apparatuses may be referred to as "Activator Methods Chiropractic Technique (AMCT)". (Further, in the field of chiropractic, chiropractic apparatuses are frequently referred to as "adjusters", because they are devices used for performing "adjustment". Therefore, hereinafter, a chiropractic apparatus is frequently referred to as an "adjuster".)

In the case of any of the above-mentioned conventional chiropractic apparatuses, the forward end of the adjuster means has either the shape of a circle or a polygon each having a relatively large surface area (for example, about 78 $mm^2$ to about 700 $mm^2$) (e.g., a circle having a diameter of about 10 mm to about 30 mm), or the shape of a circle or a polygon each having a relatively small surface area (for example, about 7 $mm^2$ to about 28 $mm^2$) (e.g., a circle having a diameter of about 3 mm to about 6 mm), wherein the circle or polygon of relatively small surface area has therearound a release surface having a predetermined tapering angle. (With respect to the former (i.e., the case of "relatively large surface area"), reference can be made to Patent Documents 1 to 4; and with respect to the latter (i.e., the case of "relatively small surface area"), reference can be made to Patent Document 5.) Such conventional chiropractic apparatuses pose problems as follows. In the case of the former prior art (i.e., the case where the forward end of the adjuster means has the shape of a circle or a polygon each having a relatively large surface area (for example, about 78 $mm^2$ to about 700 $mm^2$) (e.g., a circle having a diameter of about 10 mm to about 30 mm)), there are advantages not only in that a satisfactory force of preload can be applied to the body surface of a patient, but also in that, during the preload, the patient's pain is small and the adjuster means can be stably positioned on the body surface of the patient. However, the former prior art poses problems in that the forward end portion of the adjuster means cannot be guided to a deep region (near to a target bone for adjustment) in the body of the patient, and a thrust cannot be correctly applied to a small-area target site in the target bone. On the other hand, in the case of the latter prior art (i.e., the case where the forward end of the adjuster means has the shape of a circle or a polygon each having a relatively small surface area (for example, about 7 $mm^2$ to about 28 $mm^2$) (e.g., a circle having a diameter of about 3 mm to about 6 mm), wherein the circle or polygon has therearound a release surface having a predetermined tapering angle), there are advantages not only in that the forward end portion of the adjuster means can be guided to a deep region in the body of the patient, but also in that a thrust can be correctly applied to a small-area target site in the target bone. However, the latter prior art poses problems in that, during the preload, the patient's pain is great and it is possible to cause damage to the body surface tissue of the patient. For these reasons, in the case of the use of the above-mentioned conventional chiropractic apparatuses, performing a safe, correct and effective adjustment is not easy even for a skilled chiropractor.

There is known "Atlas Orthogonal Technique" (AOT), which is a subfield of chiropractic. In the Atlas Orthogonal Technique, the target of an adjustment is limited to the first cervical vertebra (the atlas), i.e., C1. In the case of the Atlas Orthogonal Technique, a large-sized, floor-mounted machine specialized for adjusting the atlas is used. In this large-sized, floor-mounted machine, a chiropractic apparatus (adjuster means) is attached to a movable arm which can hold the chiropractic apparatus stably. In this case, generally, the forward end of the adjuster means has the shape of a circle having a relatively small surface area (for example, a circle having a surface area of about 7 $mm^2$; that is, a circle having a diameter of about 3 mm). In the case of the use of this large-sized machine, by virtue of the fact that the chiropractic apparatus can be held stably, a skilled chiropractor can perform an adjustment of the atlas safely and relatively easily. The main reason for this is that with respect to the subcutaneous tissue around the atlas of a patient, the thickness of the fat and muscle layers therein is not great and, therefore, the forward end portion of the adjuster means can be easily guided to a region near to the atlas simply by placing relatively lightly the forward end portion of the adjuster means on the body surface of the patient. However, this large-sized machine is specialized for adjusting the atlas and cannot be used for an adjustment of a bone other than the atlas.

A chiropractic apparatus which can solve the above-mentioned problems accompanying the prior art has not yet been developed.

[Patent Document 1] U.S. Patent Application Publication No. US 2002/0082532 A1
[Patent Document 2] U.S. Pat. No. 6,379,375
[Patent Document 3] U.S. Pat. No. 6,602,211
[Patent Document 4] U.S. Pat. No. 6,805,700
[Patent Document 5] Unexamined Japanese Patent Application Laid-Open Specification No. 2009-5892
[Non-Patent Document 1] "Kairopurakutikku-Gairon (Outline of Chiropractic)", authored by Seikyo SUZUKI, published by Taniguchi Shoten Publishing Co., Japan (1987)
[Non-Patent Document 2] "Hajimete Manabu Kairopurakutikku-Sukiru-Kihon-Gensoku-Kara Manipyureishon-Sukiru-Made—(Introduction to Chiropractic Skills—from basic principles to manipulation skills)", authored and edited by David Byfield, translation supervised by Motoaki OTANI, published by IDO-NO-NIPPON SHA INC., Japan (1999)
[Non-Patent Document 3] "Okai-DC-No Tekunikku-Bukku, Kihon-Hen, Jissen-Kairopurakutikku-Ajasutomento-Tekunikku (Technique Book of Okai DC (Basics) Practical Chiropractic Adjustment Techniques)", authored by Takeshi OKAI, published by Japan Medical Publishing Co. LTD., Japan (2004)

DISCLOSURE OF THE INVENTION

Problems to Be Solved by the Invention

Thus, it has been desired to develop a chiropractic apparatus which can solve the above-mentioned problems accompanying the prior art, i.e., a chiropractic apparatus which is not only easily portable, but also enables even a chiropractor not having a high level skill to perform easily a safe, correct and effective adjustment of any bone of the entire body skeleton of a patient without causing a pain to the patient.

Means to Solve the Problems

In this situation, the present inventor has made extensive and intensive studies with a view toward solving the above-mentioned problems. As a result, he has unexpectedly found that the above-mentioned problems can be solved by a chiropractic apparatus comprising the following means (i) and (ii): (i) a chiropractic adjuster means containing a thrust member having a thrust head, and (ii) a release-surface means attached to the chiropractic adjuster means, the release-surface means having a surface for forming a release surface, wherein, when a longitudinal forward thrust is applied to the thrust member so as to give a thrust to a body surface of a patient, the release-surface means and the thrust head are subjected to relative movement with respect to each other, whereby a release surface comprising the surface for forming a release surface is formed around the thrust head, the release surface having at least a part thereof placed in contact with the body surface of the patient.

The present invention has been completed, based on this finding.

The foregoing and other objects, features and advantages of the present invention will be apparent from the following detailed description taken in connection with the accompanying drawings, and the appended claims.

Effects of the Invention

By the use of the chiropractic apparatus of the present invention capable of forming a release surface, it becomes possible that, after a target site for chiropractic treatment (adjustment) is determined by performing a palpation on a patient, a satisfactory force of preload can be applied to the body surface of the patient through a relatively large contact area which is the total surface area of the forward end portion (thrust head) of the chiropractic adjuster means and, present therearound, the surface for forming a release surface. Therefore, by virtue of the relatively large contact area, there can be obtained advantages not only in that, during the preload, the patient's pain is small and the chiropractic adjuster means can be stably positioned on the body surface of the patient without causing damage to the body surface tissue, but also in that, after the preload, a satisfactory effect of treatment (adjustment) can be achieved even when using a small force of adjustment. Further, by virtue of the formation of a release surface around the thrust head of the chiropractic adjuster means when performing an adjustment, there can be achieved advantages not only in that the thrust head of the chiropractic adjuster means can be guided to a deep region (near to a target bone for adjustment) in the body of the patient, but also in that a thrust can be correctly applied to a small-area target site in the target bone. Thus, by the use of the chiropractic apparatus of the present invention, chiropractic treatment can be performed more safely, effectively and efficiently.

BRIEF DESCRIPTION OF THE DRAWINGS

FIG. 8 is a diagrammatic cross-sectional view of still another example of the chiropractic apparatus.

DESCRIPTION OF REFERENCE NUMERALS

Figure 1A:
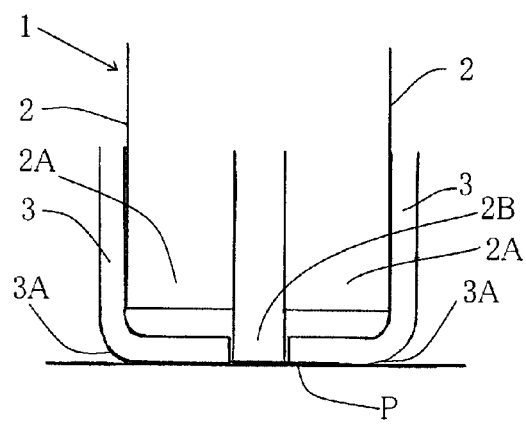
FIG. 1 is a diagrammatic cross-sectional view of an example of the chiropractic apparatus.

1 Chiropractic apparatus
2 Chiropractic adjuster means
2A Casing of a chiropractic adjuster means
2B Forward end portion (thrust head) of a chiropractic adjuster means
2C Trigger member
2D Coil compression spring
2E Thrust driving block
2F Thrust rod
2G Coil compression spring
2H Coil compression spring
3 Release-surface means
3A Surface for forming a release surface
3B Release surface
3C Hinge
P Body surface of a patient
L Left-side interface line
R Right-side interface line
X Tangent line to the right-side interface line
Y Tangent line to the left-side interface line
Z Central axis of the thrust head
θ Angle formed between the tangent line to the right-side interface line or left-side interface line and the central axis of the thrust head

BEST MODE FOR CARRYING OUT THE INVENTION

In the present invention, there is provided a chiropractic apparatus comprising the following means (i) and (ii):
(i) a chiropractic adjuster means comprising:
  a thrust member extending in a longitudinal direction of the chiropractic adjuster means and having a thrust head constituting a forward end portion of the chiropractic adjuster means,
  a driving member for applying a longitudinal forward thrust to the thrust member, and
  a trigger member for operating the driving member,
(ii) a release-surface means attached to the chiropractic adjuster means, the release-surface means having a surface for forming a release surface,
  wherein, by applying a longitudinal forward thrust to the thrust member so as to give a thrust to a body surface of a patient, the release-surface means and the thrust head are capable of relative movement with respect to each other, and
  wherein, when a longitudinal forward thrust is applied to the thrust member so as to give a thrust to the body surface of the patient to thereby subject the release-surface means and the thrust head to relative movement with respect to each other, a release surface comprising the surface for forming a release surface is formed around the thrust head, the release surface having at least a part thereof placed in contact with the body surface of the patient.

Next, for easier understanding of the present invention, the essential features and various preferred embodiments of the present invention are enumerated below.

1. A chiropractic apparatus comprising the following means (i) and (ii):
(i) a chiropractic adjuster means comprising:
  a thrust member extending in a longitudinal direction of the chiropractic adjuster means and having a thrust head constituting a forward end portion of the chiropractic adjuster means,
  a driving member for applying a longitudinal forward thrust to the thrust member, and
  a trigger member for operating the driving member,
(ii) a release-surface means attached to the chiropractic adjuster means, the release-surface means having a surface for forming a release surface,
  wherein, by applying a longitudinal forward thrust to the thrust member so as to give a thrust to a body surface of a patient, the release-surface means and the thrust head are capable of relative movement with respect to each other, and
  wherein, when a longitudinal forward thrust is applied to the thrust member so as to give a thrust to the body surface of the patient to thereby subject the release-surface means and the thrust head to relative movement with respect to each other, a release surface comprising the surface for forming a release surface is formed around the thrust head, the release surface having at least a part thereof placed in contact with the body surface of the patient.

2. The chiropractic apparatus according to item 1 above, wherein, when a longitudinal forward thrust is applied to the thrust member so as to give a thrust to the body surface of the patient, an angle formed between the release surface and the longitudinal direction of the thrust member decreases as the thrust member moves forward in the depthwise direction of the body at the body surface of the patient.

3. The chiropractic apparatus according to item 2 above, wherein the release-surface means is comprised of a material capable of changing its shape, and
  wherein, when a longitudinal forward thrust is applied to the thrust member so as to give a thrust to the body surface of the patient, the release-surface means changes its shape as the thrust member moves forward in the depthwise direction of the body at the body surface of the patient, so that the release surface formed changes its shape accordingly, thereby resulting in the decrease in the angle formed between the release surface and the longitudinal direction of the thrust member.

4. The chiropractic apparatus according to item 2 above, wherein the release-surface means is comprised of at least one flap which is pivotably attached to the periphery of a forward end of the thrust head,
  the flap being pivotable in the longitudinal direction of the thrust member,
  wherein the angle formed between the surface of the flap for forming a release surface and the longitudinal direction of the thrust member is in the range of from 90 degrees to 20 degrees.

5. The chiropractic apparatus according to item 3 above, wherein the release-surface means is comprised of a sheet made of a flexible material,
  wherein the sheet is attached to the chiropractic adjuster means so that the thrust head is covered by the sheet having its planar direction positioned perpendicular to the longitudinal direction of the thrust member, and
  wherein, when a longitudinal forward thrust is applied to the thrust member toward the body surface of the patient, the thrust head is caused to push forward the sheet, thereby forming the release surface and giving a thrust, through the sheet, to the body surface of the patient.

6. The chiropractic apparatus according to item 3 above, wherein the release-surface means is comprised of a rubber elasticity material body which is positioned so as to constitute a forward end portion of the thrust member, wherein the forward end portion is exclusive of the thrust head,
  wherein, when a longitudinal forward thrust is applied to the thrust member so as to give a thrust to the body surface of the patient, the release-surface means is compressed in the longitudinal direction of the thrust member to thereby protrude outwardly in a direction perpendicular to the longitudinal direction of the thrust member, thereby forming the release surface.

7. The chiropractic apparatus according to item 3 above, wherein the release-surface means is comprised of a rubber elasticity material body which is attached to a side surface of the thrust head,
  wherein, when a longitudinal forward thrust is applied to the thrust member so as to give a thrust to the body surface of the patient, the release-surface means is flexed as pushed back by the body surface of the patient, thereby forming the release surface.

8. The chiropractic apparatus according to item 1 above, wherein the release-surface means is positioned so as to surround the thrust head and has a forward end portion having a tapered shape.

Hereinbelow, the present invention is described in detail with reference to the accompanying drawings.

Figure 1B:
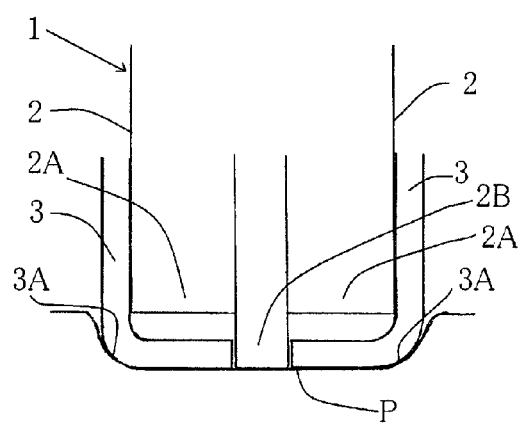
Figure 1C:
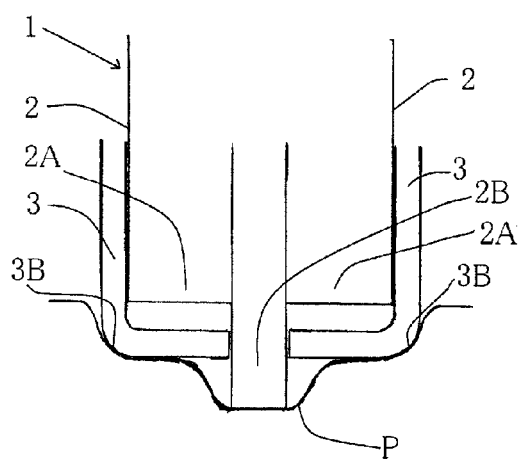

FIG. 1 is a diagrammatic cross-sectional view of an example of the chiropractic apparatus of the present invention. The item (a) of FIG. 1 shows a state where the chiropractic apparatus is placed in contact with the body surface of the patient. The item (b) of FIG. 1 shows a state where a preload is applied to the body surface of the patient. The item (c) of FIG. 1 shows a state where, after the application of a preload to the body surface of the patient, a thrust is applied to the body surface of the patient. As shown in FIG. 1, chiropractic apparatus 1 of the present invention comprises chiropractic adjuster means 2 (hereinafter, "chiropractic adjuster means" is frequently referred to simply as "adjuster means") and release-surface means 3.

Adjuster means 2 comprises:

a thrust member extending in a longitudinal direction of the chiropractic adjuster means and having thrust head 2B constituting a forward end portion of adjuster means 2, a driving member for applying a longitudinal forward thrust to the thrust member, and a trigger member for operating the driving member. Adjuster means 2 is enclosed in casing (outer covering) 2A, and thrust head 2B can be pushed out from the opening at the lower end of casing 2A. With respect to the internal structure of adjuster means 2, detailed explanation is given later.

In FIG. 1, release-surface means 3 is a cap-shaped structure having an opening at a forward end thereof, and the cap-shaped structure as release-surface means 3 is attached to adjuster means 2 so as to cover the forward end portion of adjuster means 2. The inside surface of the upper half of release-surface means 3 (i.e., the inside surface of the portion thereof extending perpendicularly to the body surface of the patient) is attached to casing 2A of adjuster means 2. This attachment can be made by conventional methods, such as adhesion and screwing (e.g., attaching release-surface means 3 to adjuster means 2 by means of a screw; and screwing release-surface means 3 to adjuster means 2). Release-surface means 3 has surface 3A for forming a release surface (see the item (a) of FIG. 1), wherein surface 3A forms release surface 3B when a thrust is applied to body surface P of the patient (see the item (c) of FIG. 1).

In the present invention, the term "release-surface means" refers to a means having a surface which is capable of forming a release surface when a longitudinal forward thrust is applied to the thrust member so as to give a thrust to the body surface of the patient. In the present invention, the term "release surface" refers to a surface of the release-surface means, which is formed when a longitudinal forward thrust is applied to the thrust member so as to give a thrust to the body surface of the patient, and which has at least a part thereof placed in contact with the body surface of the patient. The release surface may be or may not be a planar surface. Further, the release surface may have or may not have properties such that, when a longitudinal forward thrust is applied to the thrust member so as to give a thrust to the body surface of the patient, the release surface exhibits a substantial change in shape as the thrust member moves forward in the depthwise direction of the body at body surface P of the patient.

In chiropractic apparatus 1 of the present invention, by applying a longitudinal forward thrust to the thrust member of adjuster means 2 so as to give a thrust to the body surface of the patient, release-surface means 3 and thrust head 2B are capable of relative movement with respect to each other. In the embodiment shown in FIG. 1, the inside surface of the upper half of release-surface means 3 is attached to casing 2A of adjuster means 2. In this embodiment, the apparatus is designed so that, in operation of this apparatus, thrust head 2B is pushed out from the opening at the lower end of casing 2A and, hence, release-surface means 3 and thrust head 2B are capable of relative movement with respect to each other. When a longitudinal forward thrust is applied to the thrust member so as to give a thrust to body surface P of the patient to thereby subject release-surface means 3 and thrust head 2B to relative movement with respect to each other, release surface 3B comprising surface 3A for forming a release surface is formed around thrust head 2B, wherein release surface 3B has at least a part thereof placed in contact with body surface P of the patient.

Before the application of a thrust to the body surface of the patient, a preload is applied to the body surface of the patient. The item (b) of FIG. 1 shows a state where a preload is applied to the body surface of the patient. In the present invention, a satisfactory force of preload can be applied to body surface P of the patient through a relatively large contact area which is the total surface area of the forward end portion (thrust head 2B) of adjuster means 2 and, present therearound, surface 3A for forming a release surface. Therefore, by virtue of the relatively large contact area, there can be obtained advantages in that, during the preload, the patient's pain is small and the adjuster means can be stably positioned on the body surface of the patient without causing damage to the body surface tissue of the patient.

The item (c) of FIG. 1 shows a state where, after the application of a preload to the body surface of the patient, a thrust is applied to the body surface of the patient. When a longitudinal forward thrust is applied to the thrust member so as to give a thrust to body surface P of the patient, release surface 3B comprising surface 3A for forming a release surface is formed around thrust head 2B, release surface 3B having at least a part thereof placed in contact with body surface P of the patient (see the item (c) of FIG. 1). In the present invention, by virtue of the formation of release surface 3B, there can be achieved advantages not only in that the forward end portion (thrust head 2B) of adjuster means 2 can be guided to a deep region (near to a target bone for adjustment) in the body of the patient, but also in that a thrust can be correctly applied to a small-area target site in the target bone.

Thus, in the present invention, there can be obtained advantages not only in that, during the preload, the patient's pain is small and the adjuster means can be stably positioned on the body surface of the patient without causing damage to the body surface tissue, but also in that the forward end portion (thrust head 2B) of adjuster means 2 can be guided to a deep region (near to a target bone for adjustment) in the body of the patient, and a thrust can be correctly applied to a small-area target site in the target bone. Therefore, chiropractic treatment can be performed more safely, effectively and efficiently.

With respect to the shape, size and material of release-surface means 3, there is no particular limitation so long as when a longitudinal forward thrust is applied to the thrust member so as to give a thrust to body surface P of the patient, release surface 3B as described above is formed. As examples of shapes of release-surface means 3, there can be mentioned planar shapes, tapered shapes (such as the shapes shown in FIGS. 8 and 9), rounded shapes (such as the shape of a convex lens), and inverted rounded shapes (i.e., recessed spherical shapes, such as the shape of a concave lens). The material for producing release-surface means 3 may be or may not be capable of changing its shape. Examples of materials (for producing release-surface means 3) capable of shape change include flexible materials. Examples of flexible materials include cloth, flexible resins (e.g., flexible epoxy resin, flexible urethane resin, flexible acrylic resin, flexible vinyl chloride resin, flexible phenolic resin, and flexible polycarbonate resin), elastic materials (e.g., rubber elastic materials, such as silicone rubber), and soft materials. Examples of rubber elastic materials include rubber tubes sealedly containing a fluid, such as a gas (e.g., air), a liquid or a gel.

It is preferred that the area of the portion of release-surface 3B which is placed in contact with body surface P of the patient is larger than the area of the forward end of thrust head 2B. More specifically, it is preferred that the ratio represented by the formula: "the area of the portion of release-surface 3B which is placed in contact with body surface P of the patient/ the area of the forward end of thrust head 2B" is 0.8 to 58, more advantageously 8 to 36. The above-mentioned numerical range is especially preferred when the angle formed between release surface 3B and the longitudinal direction of the thrust member is 90 degrees (as in the embodiment shown in FIG. 1).

Figure 2A:
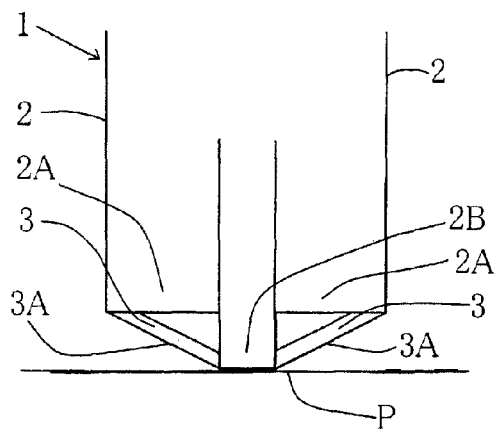
FIG. 2 is a diagrammatic cross-sectional view of another example of the chiropractic apparatus.
Figure 2B:
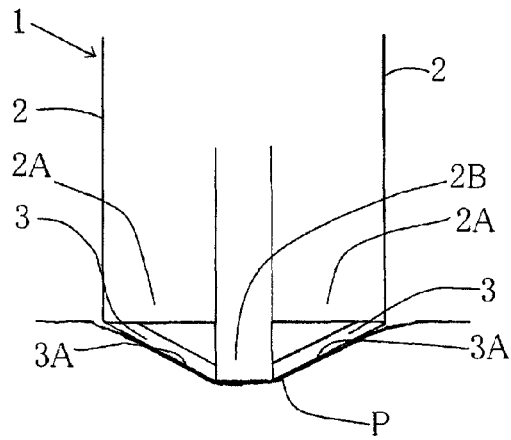
Figure 2C:
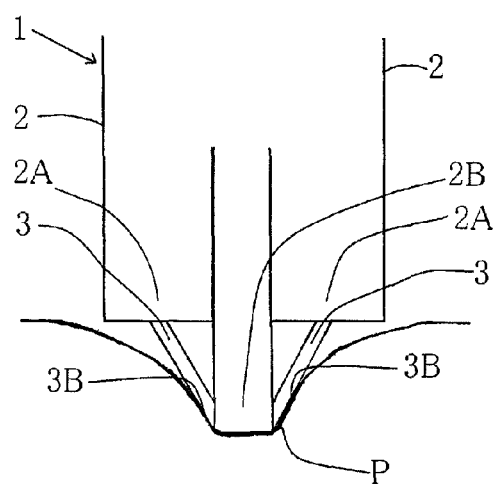

FIG. 2 shows a diagrammatic cross-sectional view of another example of the chiropractic apparatus of the present invention. The item (a) of FIG. 2 shows a state where the chiropractic apparatus is placed in contact with the body surface of the patient. The item (b) of FIG. 2 shows a state where a preload is applied to the body surface of the patient. The item (c) of FIG. 2 shows a state where, after the application of a preload to the body surface of the patient, a thrust is applied to the body surface of the patient.

Adjuster means 2 shown in FIG. 2 is the same as adjuster means 2 shown in FIG. 1.

If it is intended to explain the structure of release-surface means 3 in FIG. 2 by comparing it to the structure of an umbrella, release-surface means 3 may be said to be a structure such that the thrust member is disposed at the same position as the central shaft of the umbrella, and release-surface means 3 is disposed at the same position as the openable/closable canopy of the umbrella. The lower end of this structure (release-surface means 3) is attached to thrust head 2B. The attachment of the lower end of the structure to thrust head 2B can be made by conventional methods, such as adhesion and screwing (e.g., attaching the lower end to thrust head 2B by means of a screw; and screwing the lower end to thrust head 2B). The upper end of the structure is secured to the lower end of casing 2A so as to be movable in a horizontal direction.

In the embodiment shown in FIG. 2, the chiropractic apparatus has a construction such that, when a longitudinal forward thrust is applied to the thrust member so as to give a thrust to body surface P of the patient, an angle formed between release surface 3B and the longitudinal direction of the thrust member decreases as the thrust member moves forward in the depthwise direction of the body at body surface P of the patient (see the item (c) of FIG. 2). By virtue of this construction, the forward end portion (thrust head 2B) of adjuster means 2 can be guided to a deeper region (nearer to a target bone for adjustment) in the body of the patient, and a thrust can be given more correctly to a small-area target site in the target bone. With respect to the angle formed between release surface 3B and the longitudinal direction of the thrust member, the amount of the angle decrease caused when the trust is given is preferably 10 degrees or more, more preferably 15 degrees or more. With respect to the minimum value of the angle after the decrease, there is no particular limitation. However, the angle after the decrease is generally about 15 degrees. For example, an initial angle in the range of from 90 degrees to 20 degrees may be decreased to an angle of 15 degrees. In this case, the amount of the angle decrease is in the range of from 75 degrees to 5 degrees.

In the embodiment shown in FIG. 2, the angle formed between release surface 3B and the longitudinal direction of the thrust member decreases to a satisfactory level (e.g., to an angle of about 15 degrees) as the thrust member moves forward in the depthwise direction of the body at body surface P of the patient. Therefore, the forward end portion (thrust head 2B) of adjuster means 2 can be guided to a deeper region (nearer to a target bone for adjustment) in the body of the patient, and a thrust can be given more correctly to a small-area target site in the target bone.

Figure 13:
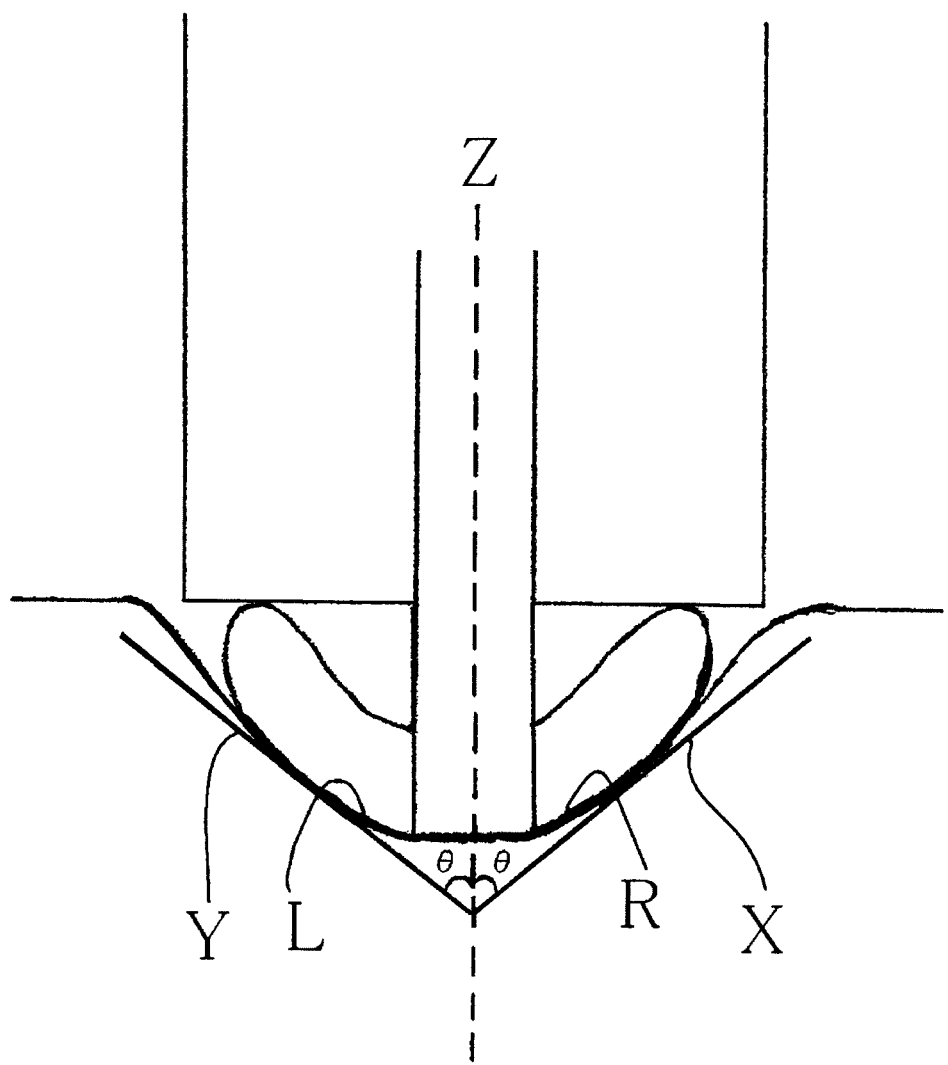
FIG. 13 is an explanatory view showing the definition of the angle formed between the release surface and the longitudinal direction of the thrust member.

The angle formed between release surface 3B and the longitudinal direction of the thrust member is defined as follows. Consider a cross-sectional view as shown in the item (c) of any of FIGS. 1 to 11. In such a cross-sectional view, the portion where release surface 3B and body surface P of the patient are contacted with each other (i.e., the interface between release surface 3B and body surface P of the patient) forms a line (a straight or curved line). This interface line is divided by the central axis of thrust head 2B into two segments, i.e., the right-side interface line and the left-side interface line. An average value is obtained with respect to the angle formed between the right-side interface line and the central axis of thrust head 2B, and the angle formed between the left-side interface line and the central axis of thrust head 2B. The resultant average value of the two angles is defined to be the angle formed between release surface 3B and the longitudinal direction of the thrust member. When the right-side interface line is not a straight line but a curved line, the angle formed between the right-side interface line and the central axis of thrust head 2B is defined as follows. Explanation is given with reference to FIG. 13 (which is concerned with the embodiment shown in FIG. 7 and in which the reference numerals for the chiropractic apparatus and the like are omitted). Consider tangent line X to right-side interface line R at a middle point on line R, wherein the middle point means the point at half the distance from one end to the other end of right-side interface line R, as measured along the curvature of line R. Angle θ formed between tangent line X and central axis Z of thrust head 2B is defined to be the angle formed between right-side interface line R and central axis Z of thrust head 2B. When the left-side interface line is not a straight line but a curved line, the angle formed between the left-side interface line and the central axis of thrust head 2B is defined in the same way as in the case where the right-side interface line is not a straight line but a curved line. (In FIG. 13, the angle formed between right-side interface line R and central axis Z of thrust head 2B is equal to the angle formed between left-side interface line L and central axis Z of thrust head 2B.) In this connection, it should be noted that when right-side interface line R and left-side interface line L are symmetrical with respect to central axis Z of thrust head 2B (as in the case of release surface 3B shown in the item (c) of any of FIGS. 1 to 11), the angle formed between right-side interface line R and central axis Z of thrust head 2B is equal to the angle formed between left-side interface line L and central axis Z of thrust head 2B, so that the angle formed between right-side interface line R and central axis Z of thrust head 2B is the angle formed between release surface 3B and the longitudinal direction of the thrust member.

In practice, the above-defined angle formed between release surface 3B and the longitudinal direction of the thrust member can be measured as follows. A chiropractic treatment is performed on the body surface of the patient (the treatment may alternatively be performed on an object (as a dummy of the patient) made of a material having the same physical characteristics as the body surface and subcutaneous tissue of the patient). During the chiropractic treatment, an MRI (magnetic resonance imaging) or a CT (computed tomography) is performed to thereby obtain a cross-sectional view (i.e., image) as shown in the item (c) of any of FIGS. 1 to 11. Using the thus-obtained cross-sectional view, the angle is measured in accordance with the above definition of the angle. In this connection, it should be noted that in the case as shown in the item (c) of any of FIGS. 1 to 5, i.e., in the case where each of right-side interface line R and left-side interface line L is a straight line, the above-defined angle can be obtained simply by a calculation using the distance through which thrust head 2B is moved forward, and hence there is no need for performing any actual chiropractic treatment.

Figure 3A:
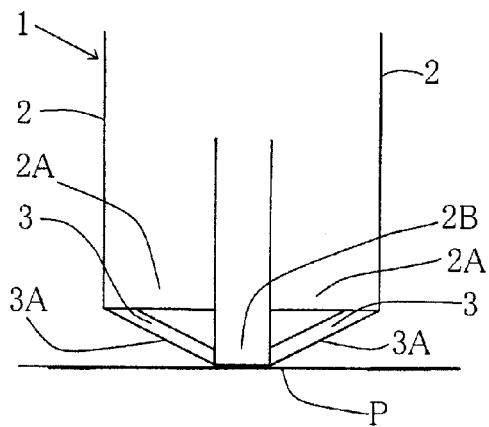
FIG. 3 is a diagrammatic cross-sectional view of still another example of the chiropractic apparatus.
Figure 3B:
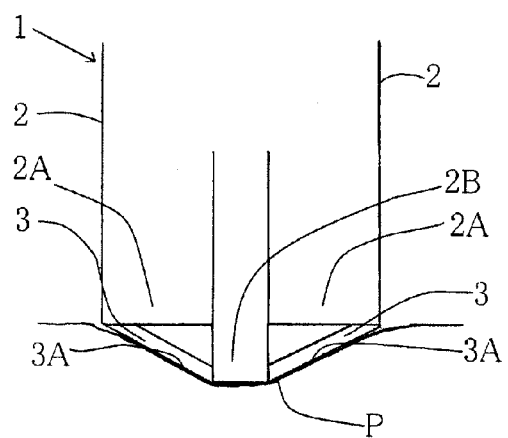
Figure 3C:
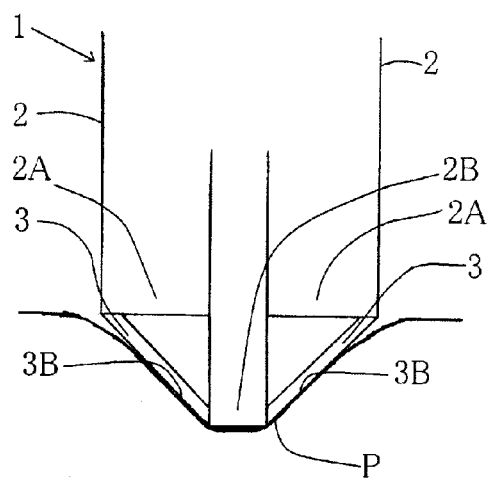

FIG. 3 is a diagrammatic cross-sectional view of still another example of the chiropractic apparatus of the present invention. The item (a) of FIG. 3 shows a state where the chiropractic apparatus is placed in contact with the body surface of the patient. The item (b) of FIG. 3 shows a state where a preload is applied to the body surface of the patient. The item (c) of FIG. 3 shows a state where, after the application of a preload to the body surface of the patient, a thrust is applied to the body surface of the patient.

Adjuster means 2 shown in FIG. 3 is the same as adjuster means 2 shown in FIG. 1.

Release-surface means 3 shown in FIG. 3 is a structure having the shape of a side surface of an inverted circular truncated cone and is comprised of a material capable of changing its shape. The lower end portion of this structure is attached to thrust head 2B, and the upper end portion of this structure is attached to the lower end of casing 2A. In this embodiment, the apparatus is designed so that this structure as release-surface means 3 is capable of changing its shape and, hence, release-surface means 3 and thrust head 2B are capable of relative movement with respect to each other. The attachment of release-surface means 3 to thrust head 2B and casing 2A can be made by conventional methods, such as adhesion and screwing (e.g., attaching release-surface means 3 to adjuster means 2 by means of a screw; and screwing release-surface means 3 to adjuster means 2).

In the embodiment shown in FIG. 3, the chiropractic apparatus has a construction such that, when a longitudinal forward thrust is applied to the thrust member so as to give a thrust to body surface P of the patient, release-surface means 3 changes its shape as the thrust member moves forward in the depthwise direction of the body at body surface P of the patient, so that release surface 3B formed changes its shape accordingly. Similarly to the embodiment shown in FIG. 2, such a change in the shape of release surface 3B results in the decrease in the angle formed between release surface 3B and the longitudinal direction of the thrust member. As examples of such release-surface means 3, there can be mentioned those made of an elastic material (such as a flexible sheet or a rubber elastic material). Examples of rubber elastic materials include rubber tubes sealedly containing a fluid, such as a gas (e.g., air), a liquid or a gel.

Figure 4A:
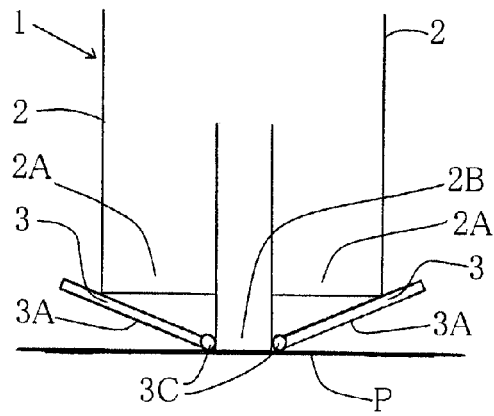
FIG. 4 is a diagrammatic cross-sectional view of still another example of the chiropractic apparatus.
Figure 4B:
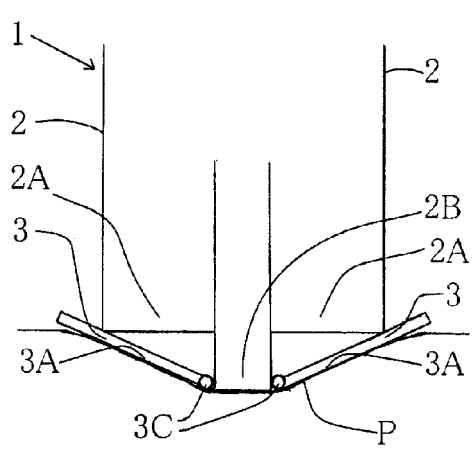
Figure 4C:
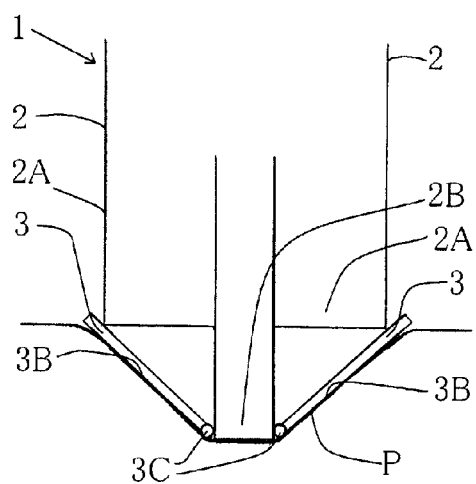

FIG. 4 is a diagrammatic cross-sectional view of still another example of the chiropractic apparatus of the present invention. The item (a) of FIG. 4 shows a state where the chiropractic apparatus is placed in contact with the body surface of the patient. The item (b) of FIG. 4 shows a state where a preload is applied to the body surface of the patient. The item (c) of FIG. 4 shows a state where, after the application of a preload to the body surface of the patient, a thrust is applied to the body surface of the patient.

Adjuster means 2 shown in FIG. 4 is the same as adjuster means 2 shown in FIG. 1.

Release-surface means 3 shown in FIG. 4 is comprised of at least one flap (2 flaps are shown in FIG. 4). The flap has, at its forward end, hinge 3C and is pivotably attached to the periphery of a forward end of thrust head 2B through hinge 3C. The upper portion of the flap is movably held by casing 2A, wherein the movable holding is made at a portion of the flap close to the upper end of the flap. The angle formed between surface 3A of the flap for forming a release surface and the longitudinal direction of the thrust member is in the range of from 90 degrees to 20 degrees. The flap is arranged in a manner such that, when a longitudinal forward thrust is applied to the thrust member so as to give a thrust to body surface P of the patient, the angle formed between release surface 3B (formed from surface 3A of the flap for forming a release surface) and the longitudinal direction of the thrust member decreases. Such a decrease in the angle is preferably 10 degrees or more, more preferably 15 degrees or more. With respect to the minimum value of the angle after the decrease, there is no particular limitation, but it is generally about 15 degrees. For example, an initial angle in the range of from 90 degrees to 20 degrees may be decreased to an angle of 15 degrees. In this case, the amount of the angle decrease is in the range of from 75 degrees to 5 degrees.

In the embodiment shown in FIG. 4, as the thrust member moves forward in the depthwise direction of the body at body surface P of the patient, the angle formed between release surface 3B and the longitudinal direction of the thrust member decreases to a satisfactory level (for example, to an angle of about 15 degrees). Therefore, there can be achieved advantages not only in that the forward end portion (thrust head 2B) of adjuster means 2 can be guided to a deeper region (nearer to a target bone for adjustment) in the patient body, but also in that a thrust can be more correctly applied to a small-area target site in the target bone.

Figure 5A:
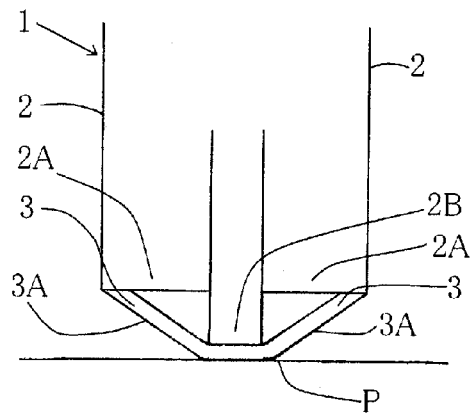
FIG. 5 is a diagrammatic cross-sectional view of still another example of the chiropractic apparatus.
Figure 5B:
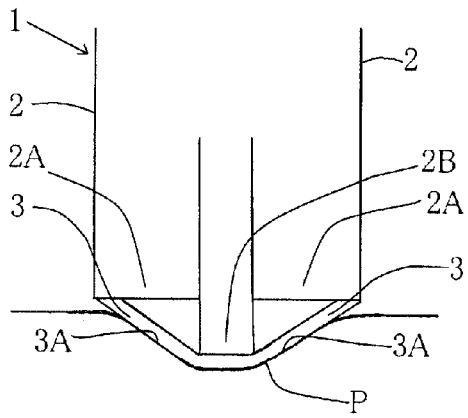
Figure 5C:
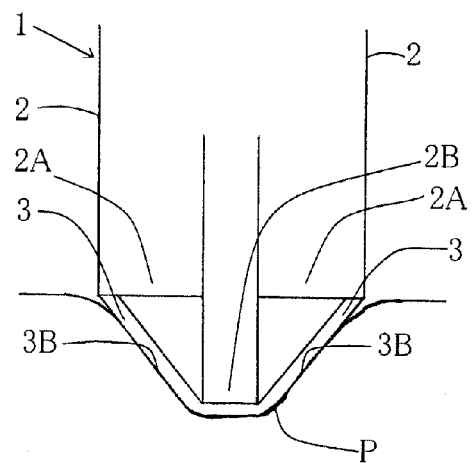

FIG. 5 is a diagrammatic cross-sectional view of still another example of the chiropractic apparatus of the present invention. The item (a) of FIG. 5 shows a state where the chiropractic apparatus is placed in contact with the body surface of the patient. The item (b) of FIG. 5 shows a state where a preload is applied to the body surface of the patient. The item (c) of FIG. 5 shows a state where, after the application of a preload to the body surface of the patient, a thrust is applied to the body surface of the patient.

Adjuster means 2 shown in FIG. 5 is the same as adjuster means 2 shown in FIG. 1.

Release-surface means 3 shown in FIG. 5 is comprised of a sheet made of a flexible material, and the sheet is attached to chiropractic adjuster means 2 so that thrust head 2B is covered by the sheet having its planar direction positioned perpendicular to the longitudinal direction of the thrust member (i.e., the central portion of the sheet is attached to thrust head 2B, and the periphery of the sheet is attached to casing 2A). The attachment of the sheet can be made by conventional methods, such as adhesion and screwing (e.g., attaching release-surface means 3 to adjuster means 2 by means of a screw; and screwing release-surface means 3 to adjuster means 2). Since release-surface means 3 is capable of changing its shape, release-surface means 3 and thrust head 2B are capable of relative movement with respect to each other. The sheet is arranged in a manner such that, when a longitudinal forward thrust is applied to the thrust member toward body surface P of the patient, thrust head 2B is caused to push forward the sheet, thereby forming release surface 3B and giving a thrust, through the sheet, to body surface P of the patient.

In the embodiment shown in FIG. 5, by the use of a sheet as release-surface means 3, it becomes possible to apply a preload to a larger surface area of body surface P of the patient. Moreover, the patient's pain during the preload can become smaller, because thrust head 2B is covered by the sheet used as release-surface means 3 and, therefore, only the sheet is placed in contact with the body surface of the patient.

Figure 6A:
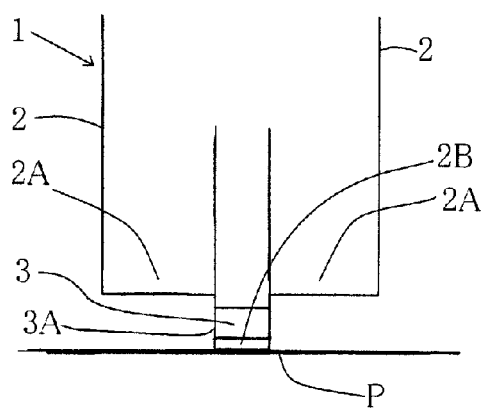
FIG. 6 is a diagrammatic cross-sectional view of still another example of the chiropractic apparatus.
Figure 6B:
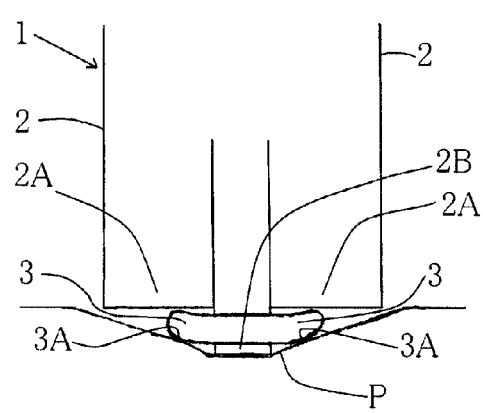
Figure 6C:
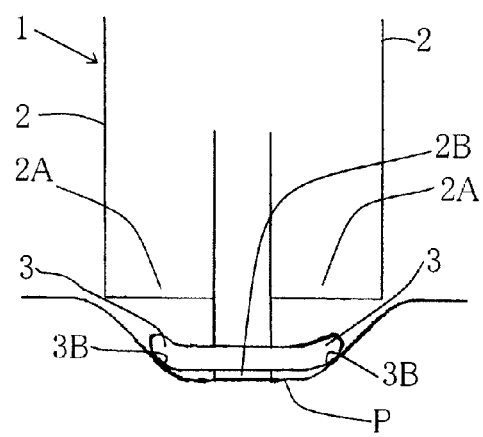

FIG. 6 is a diagrammatic cross-sectional view of still another example of the chiropractic apparatus of the present invention. The item (a) of FIG. 6 shows a state where the chiropractic apparatus is placed in contact with the body surface of the patient. The item (b) of FIG. 6 shows a state where a preload is applied to the body surface of the patient. The item (c) of FIG. 6 shows a state where, after the application of a preload to the body surface of the patient, a thrust is applied to the body surface of the patient.

Adjuster means 2 shown in FIG. 6 is the same as adjuster means 2 shown in FIG. 1.

Release-surface means 3 shown in FIG. 6 is comprised of a rubber elasticity material body which is positioned so as to constitute a forward end portion of the thrust member, wherein the forward end portion is exclusive of thrust head 2B. The thus positioned rubber elasticity material body may be attached to the thrust member by conventional methods, such as adhesion and screwing (e.g., attaching release-surface means 3 to adjuster means 2 by means of a screw; and screwing release-surface means 3 to adjuster means 2). Since release-surface means 3 is capable of changing its shape, release-surface means 3 and thrust head 2B are capable of relative movement with respect to each other. The release-surface means 3 has a structure such that, when a longitudinal forward thrust is applied to the thrust member so as to give a thrust to body surface P of the patient, release-surface means 3 is compressed in the longitudinal direction of the thrust member to thereby protrude outwardly in a direction perpendicular to the longitudinal direction of the thrust member, thereby forming release surface 3B.

In the embodiment shown in FIG. 6, the patient's pain during the preload becomes smaller by virtue of the use of the rubber elasticity material body as release-surface means 3.

Figure 7A:
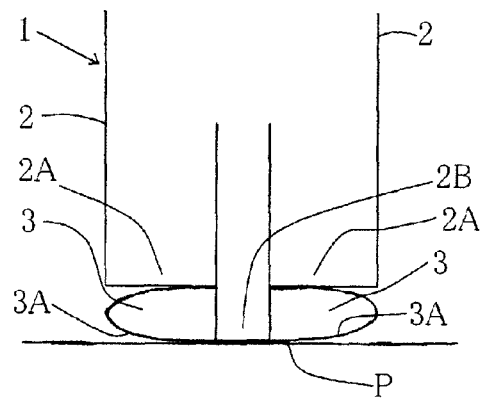
FIG. 7 is a diagrammatic cross-sectional view of still another example of the chiropractic apparatus.
Figure 7B:
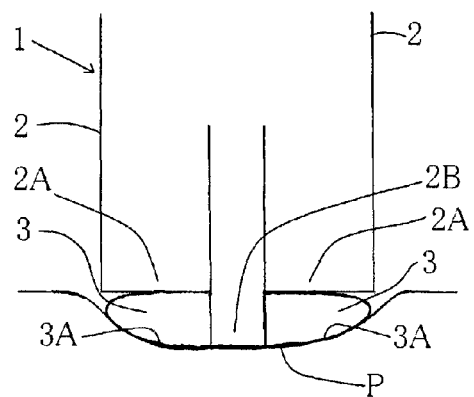
Figure 7C:
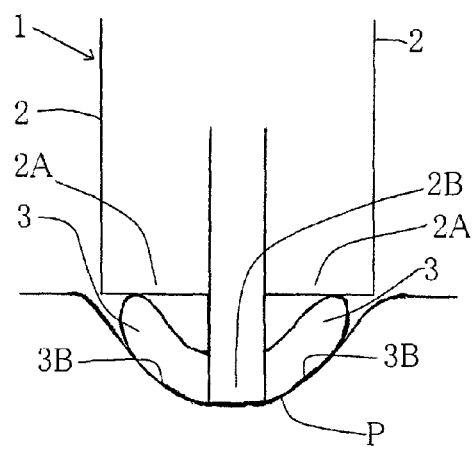

FIG. 7 is a diagrammatic cross-sectional view of still another example of the chiropractic apparatus of the present invention. The item (a) of FIG. 7 shows a state where the chiropractic apparatus is placed in contact with the body surface of the patient. The item (b) of FIG. 7 shows a state where a preload is applied to the body surface of the patient. The item (c) of FIG. 7 shows a state where, after the application of a preload to the body surface of the patient, a thrust is applied to the body surface of the patient.

Adjuster means 2 shown in FIG. 7 is the same as adjuster means 2 shown in FIG. 1.

Release-surface means 3 shown in FIG. 7 is comprised of a rubber elasticity material body which is attached to a side surface of thrust head 2B. The attachment of release-surface means 3 to the side surface of thrust head 2B can be made by conventional methods, such as adhesion and screwing (e.g., attaching release-surface means 3 to adjuster means 2 by means of a screw; and screwing release-surface means 3 to adjuster means 2). Since this release-surface means 3 is capable of changing its shape, release-surface means 3 and thrust head 2B are capable of relative movement with respect to each other. The apparatus of this embodiment is so designed that, by applying a longitudinal forward thrust to the thrust member so as to give a thrust to body surface P of the patient, release-surface means 3 is flexed as pushed back by body surface P of the patient, thereby forming release surface 3B.

In the embodiment shown in FIG. 7, since release-surface means 3 is comprised of a rubber elasticity material body, the patient's pain becomes smaller during the application of the preload.

FIG. 8 is a diagrammatic cross-sectional view of still another example of the chiropractic apparatus of the present invention. The item (a) of FIG. 8 shows a state where the chiropractic apparatus is placed in contact with the body surface of the patient. The item (b) of FIG. 8 shows a state where a preload is applied to the body surface of the patient. The item (c) of FIG. 8 shows a state where, after the application of a preload to the body surface of the patient, a thrust is applied to the body surface of the patient.

Adjuster means 2 shown in FIG. 8 is the same as adjuster means 2 shown in FIG. 1.

Release-surface means 3 shown in FIG. 8 is a structure having the shape of an inverted circular truncated cone, and the central axial portion of the inverted circular truncated cone is hollow so that the lower end portion of adjuster means 2, together with casing 2A, can be enclosed in the central axial hollow of release-surface means 3. The inside surface of release-surface means 3 having an inverted circular truncated cone shape is attached to casing 2A of adjuster means 2. This attachment of the inside surface of release-surface means 3 to casing 2A can be effected by conventional methods, such as adhesion and screwing (e.g., attaching release-surface means 3 to casing 2A by means of a screw; and screwing release-surface means 3 to casing 2A). The forward end portion of release-surface means 3 has a tapered shape. In the embodiment shown in FIG. 8, release-surface means 3 is positioned so as to surround thrust head 2B while leaving a space therebetween.

In the embodiment shown in FIG. 8, the inside surface of release-surface means 3 is attached to casing 2A of adjuster means 2. In this embodiment, the apparatus is designed so that, in operation of this apparatus, thrust head 2B is pushed out from the opening at the lower end of casing 2A and, hence, release-surface means 3 and thrust head 2B are capable of relative movement with respect to each other. When a longitudinal forward thrust is applied to the thrust member so as to give a thrust to body surface P of the patient to thereby subject release-surface means 3 and thrust head 2B to relative movement with respect to each other, release surface 3B comprising surface 3A for forming a release surface is formed around thrust head 2B, wherein release surface 3B has at least a part thereof placed in contact with body surface P of the patient.

Figure 9A:
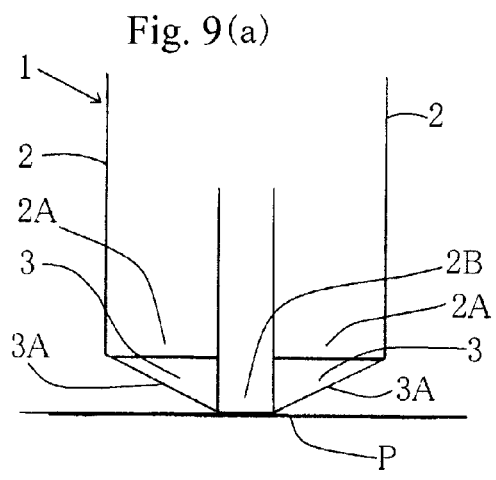
FIG. 9 is a diagrammatic cross-sectional view of still another example of the chiropractic apparatus.
Figure 9B:
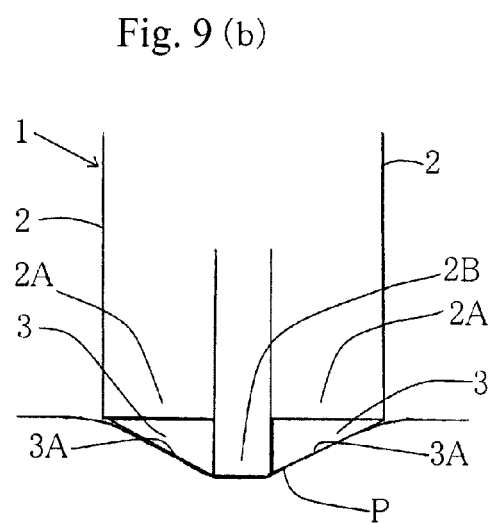
Figure 9C:
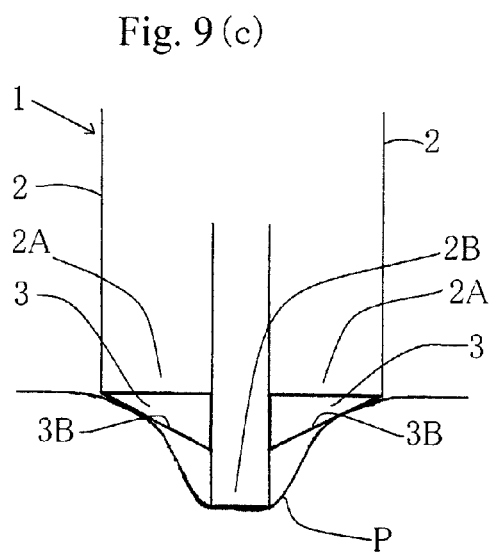

FIG. 9 is a diagrammatic cross-sectional view of still another example of the chiropractic apparatus of the present invention. The item (a) of FIG. 9 shows a state where the chiropractic apparatus is placed in contact with the body surface of the patient. The item (b) of FIG. 9 shows a state where a preload is applied to the body surface of the patient. The item (c) of FIG. 9 shows a state where, after the application of a preload to the body surface of the patient, a thrust is applied to the body surface of the patient.

Adjuster means 2 shown in FIG. 9 is the same as adjuster means 2 shown in FIG. 1.

Release-surface means 3 shown in FIG. 9 is a structure having the shape of an inverted circular truncated cone, and the central axial portion of the inverted circular truncated cone is hollow so that thrust head 2B can be inserted into the central axial hollow of release-surface means 3. Thus, release-surface means 3 is positioned so as to surround thrust head 2B. Release-surface means 3 (with the shape of an inverted circular truncated cone) has a forward end portion having a tapered shape. The upper end portion of release-surface means 3 is attached to casing 2A of adjuster means 2. This attachment can be made by conventional methods, such as adhesion and screwing (e.g., attaching release-surface means 3 to adjuster means 2 by means of a screw; and screwing release-surface means 3 to adjuster means 2).

In the embodiment shown in FIG. 9, the upper end of release-surface means 3 is attached to casing 2A of adjuster means 2. In this embodiment, the apparatus is designed so that, in operation of this apparatus, thrust head 2B is pushed out from the opening at the lower end of casing 2A and, hence, release-surface means 3 and thrust head 2B are capable of relative movement with respect to each other. When a longitudinal forward thrust is applied to the thrust member so as to give a thrust to body surface P of the patient to thereby subject release-surface means 3 and thrust head 2B to relative movement with respect to each other, release surface 3B comprising surface 3A for forming a release surface is formed around thrust head 2B, wherein release surface 3B has at least a part thereof placed in contact with body surface P of the patient.

Figure 10A:
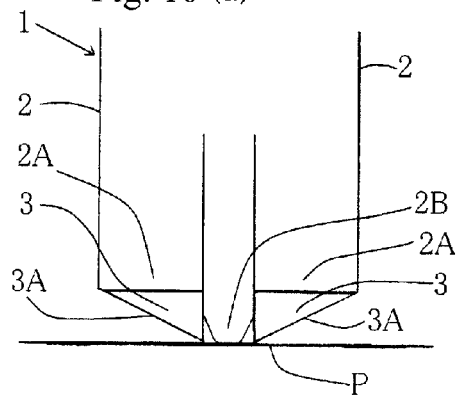
FIG. 10 is a diagrammatic cross-sectional view of still another example of the chiropractic apparatus.
Figure 10B:
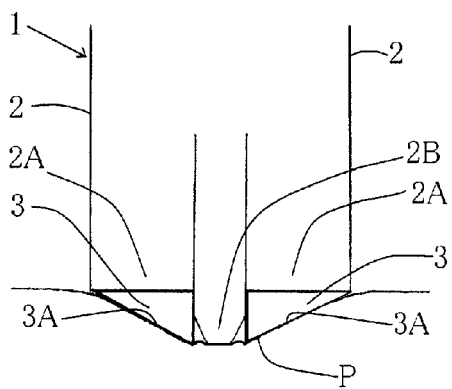
Figure 10C:
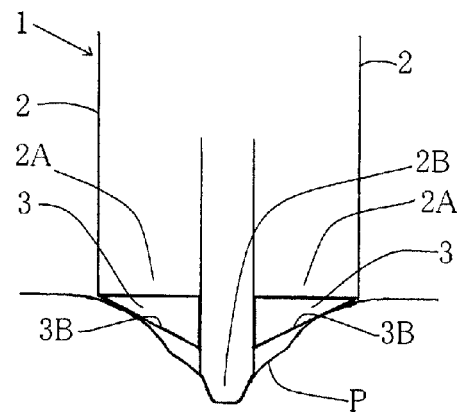

FIG. 10 is a diagrammatic cross-sectional view of still another example of the chiropractic apparatus of the present invention. The item (a) of FIG. 10 shows a state where the chiropractic apparatus is placed in contact with the body surface of the patient. The item (b) of FIG. 10 shows a state where a preload is applied to the body surface of the patient. The item (c) of FIG. 10 shows a state where, after the application of a preload to the body surface of the patient, a thrust is applied to the body surface of the patient.

Adjuster means 2 shown in FIG. 10 is the same as adjuster means 2 shown in FIG. 1 except that thrust head 2B of adjuster means 2 shown in FIG. 10 has a tapered shape at the forward end portion thereof. Release-surface means 3 shown in FIG. 10 is the same as release-surface means 3 shown in FIG. 9.

Figure 11A:
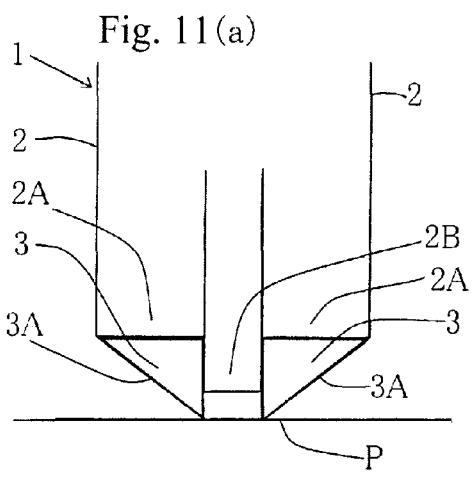
FIG. 11 is a diagrammatic cross-sectional view of still another example of the chiropractic apparatus.
Figure 11B:
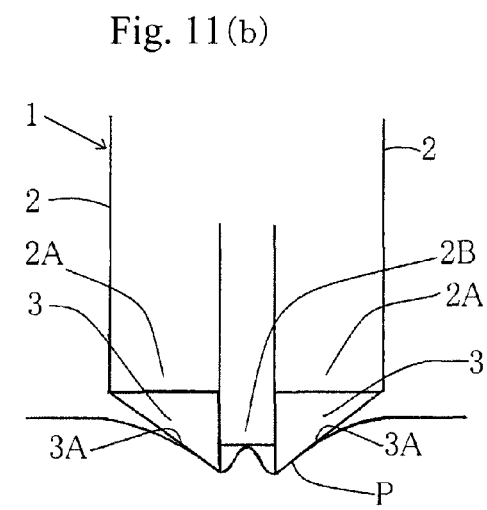
Figure 11C:
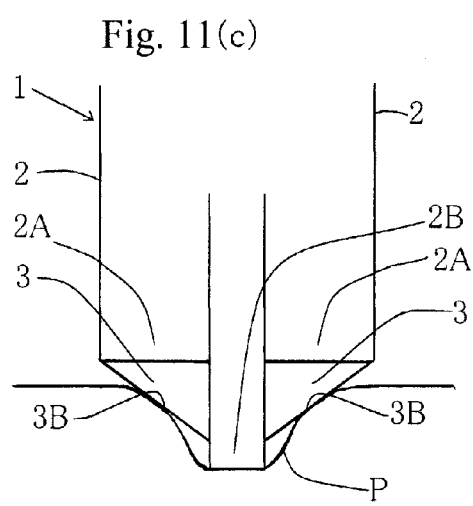

FIG. 11 is a diagrammatic cross-sectional view of still another example of the chiropractic apparatus of the present invention. The item (a) of FIG. 11 shows a state where the chiropractic apparatus is placed in contact with the body surface of the patient. The item (b) of FIG. 11 shows a state where a preload is applied to the body surface of the patient. The item (c) of FIG. 11 shows a state where, after the application of a preload to the body surface of the patient, a thrust is applied to the body surface of the patient.

Adjuster means 2 shown in FIG. 11 is the same as adjuster means 2 shown in FIG. 1. Release-surface means 3 shown in FIG. 11 is a structure having the shape of an inverted circular truncated cone as in the case of release-surface means 3 shown in FIG. 9. However, release-surface means 3 shown in FIG. 11 has its forward end portion protruding beyond thrust head 2B so that, when the chiropractic apparatus is placed in contact with the body surface of the patient, only release-surface means 3 contacts the body surface of the patient while not causing thrust head 2B to contact the body surface of the patient (see the item (a) of FIG. 11). This is the difference between release-surface means 3 shown in FIG. 11 and release-surface means 3 shown in FIG. 9. However, even in the case of the embodiment of FIG. 11, when a preload is applied to the body surface of the patient, thrust head 2B may be caused to contact the body surface of the patient (see the item (b) of FIG. 11).

Release-surface means 3 may be any combination of the above-described embodiments including the embodiments of FIGS. 1 to 11.

Explanation is made hereinbelow on chiropractic adjuster means 2. Chiropractic adjuster means 2 comprises:

a thrust member extending in a longitudinal direction of the chiropractic adjuster means and having a thrust head constituting a forward end portion of the chiropractic adjuster means, a driving member for applying a longitudinal forward thrust to the thrust member, and a trigger member for operating the driving member. Chiropractic adjuster means 2 used in the chiropractic apparatus of the present invention may have substantially the same basic structure, action mechanism and function as those of a conventional portable chiropractic apparatus, such as a so-called "activator". Therefore, adjuster means 2 may be produced using the same design information and production materials as those of a conventional chiropractic apparatus which is disclosed, for example, in any of the above-mentioned Patent Documents 1 to 4.

Figure 12:
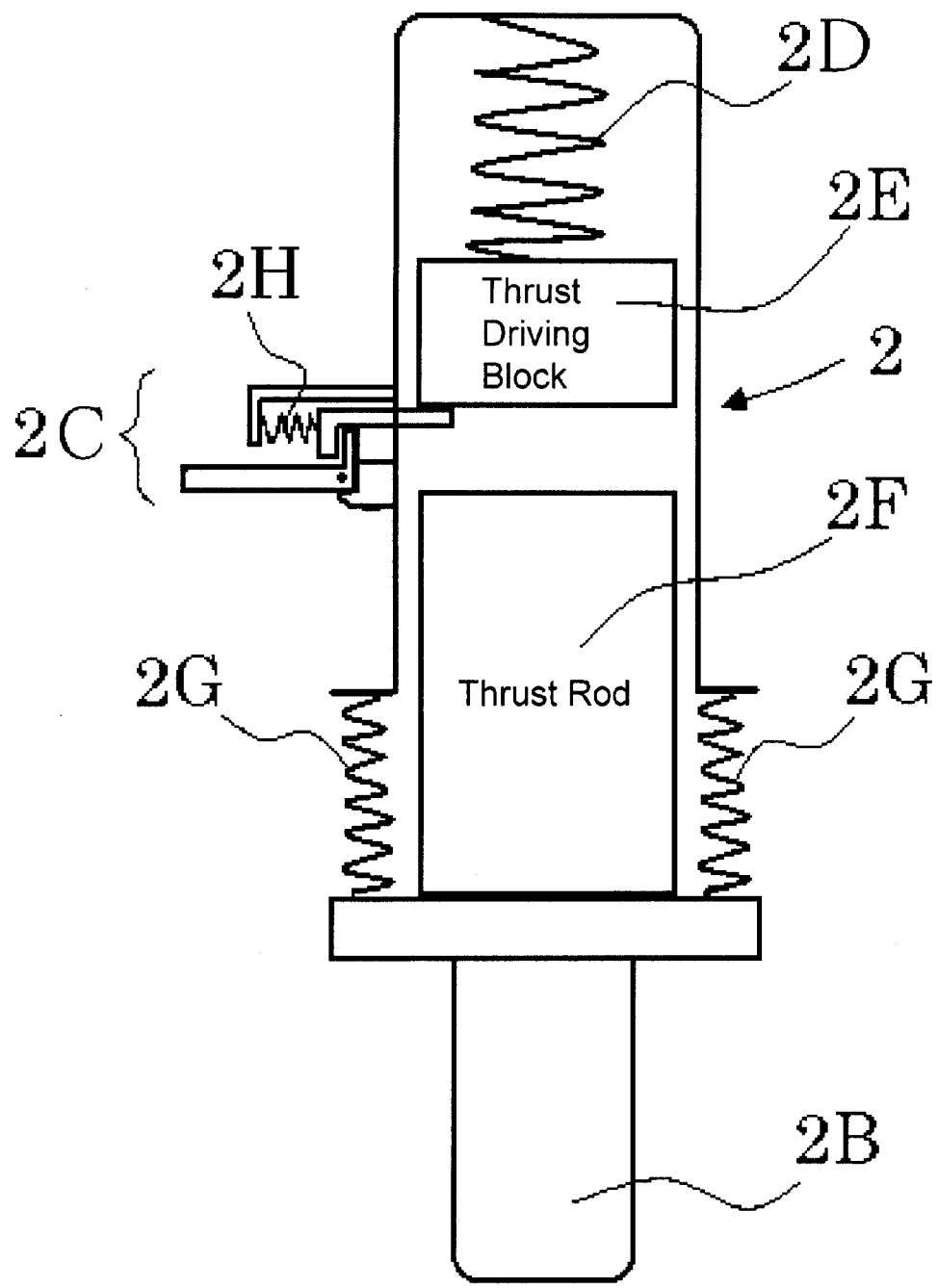
FIG. 12 is a diagrammatic view showing the internal structure of an example of a chiropractic adjuster means.

FIG. 12 is a diagrammatic view showing the internal structure of an example of chiropractic adjuster means 2. In FIG. 12, the casing of adjuster means 2 is omitted. Adjuster means 2 shown in FIG. 12 comprises thrust head 2B, trigger member 2C, coil compression spring 2D, thrust driving block 2E, thrust rod 2F, and coil compression spring 2G. Trigger member 2C contains coil compression spring 2H. Coil compression spring 2D and thrust driving block 2E constitute the driving member for applying a longitudinal forward thrust to the thrust member. Thrust rod 2F and thrust head 2B are integral with each other so as to constitute the thrust member. Coil compression spring 2G serves as a cushion which can be compressed when the forward end portion (thrust head 2B) of adjuster means 2 is pressed onto an object (such as the body surface of the patient). Thus, for example, even when adjuster means 2 as a whole is secured at a certain position, a downward movement of the forward end portion (thrust head 2B) of adjuster means 2 can be achieved, because the thrust member (comprising thrust rod 2F and thrust head 2B) is capable of moving alone by virtue of the cushioning function of coil compression spring 2G. Adjuster means 2 as shown in FIG. 12 has a structure such that, by the driving member comprising coil compression spring 2D and thrust driving block 2E, the thrust member comprising thrust rod 2F and thrust head 2B is capable of moving forward (moving macroscopically) in the longitudinal direction thereof within the extension limit of coil compression spring 2G. Such structure is generally employed in the above-mentioned so-called "activator".

By pulling trigger member 2C, adjuster means 2 is brought into action to thereby apply a thrust to the body surface of the patient. As an example of a method for pulling trigger member 2C, there can be mentioned a method in which a trigger means (not shown) capable of being engaged with a finger of the user is connected with trigger member 2C through a wire, and trigger member 2C is pulled by moving the trigger means with the user's finger. The user's finger to be engaged with the trigger means may be the same as or different from the finger used for palpation.

As another method for pulling trigger member 2C, there can be mentioned a method in which a wired or wireless communication means (not shown) is connected to trigger member 2C, and a switch (electronic trigger means) is turned on via the wired or wireless communication means to pull trigger member 2C. When this switch (electronic trigger means) is a foot switch device, the switching operation can be carried out with the user's foot.

With respect to the devices used for operating trigger member 2C of adjuster means 2 via the wired or wireless communication (i.e., wired or wireless communication means connected to trigger member 2C and a switch (electronic trigger means) to be used therewith), such devices can be easily produced based on the known electric/electronic engineering techniques applied in various fields or may be ones which are easily commercially available. As well known, due to the spreading application of advanced electrocommunication technology of recent years, very small high-performance electrocommunication devices or actuators for remote control or manipulation are widely applied as parts embedded in electric/electronic equipment of various fields. As an example of commercially available devices for wired remote control, there can be mentioned "TGA-mini" manufactured and sold by TOKI Corporation, Japan. Examples of available manufacturers capable of the services of designing and manufacturing devices for wired or wireless remote control include Kosugi Giken Co., Ltd., Japan, Osaka Jido Denki, Co., Ltd., Japan, and Itec Corporation, Japan. Thus, with respect to the electric/electronic devices or parts of relatively small sizes which are necessary for wired or wireless remote control of trigger member 2C used in the present invention, such devices or parts can be easily produced by applying the known technologies for wired or wireless remote control or manipulation, or such devices or parts may be easily commercially available, and, if desired, there are available manufacturers capable of the services of designing and producing such devices or parts.

The structure and action mechanism of adjuster means 2 are not limited to those shown in FIG. 12. For example, as to the action mechanism, adjuster means 2 can be driven by any known mechanisms applied in the art for driving chiropractic adjusters, which use various driving forces, such as air or oil pressure, electromagnetic force and human power.

With respect to the materials used for producing chiropractic adjuster means 2, there is no particular limitation so long as the object of the present invention can be achieved. It is preferred that the coil compression spring of adjuster means 2 is made of a metal (e.g., a steel). Other parts of adjuster means 2 may be made of, for example, plastics (such as a vinyl chloride resin, an acrylic resin, polypropylene and polycarbonate), steels including a stainless steel, and aluminum.

Explained hereinbelow is the method for operating the chiropractic apparatus of the present invention (i.e., the method for performing a chiropractic treatment by using the chiropractic apparatus of the present invention).

First, body surface P of the patient is palpated with the tip of a finger of the user while pulling the skin of the portion of the body surface (and portions therearound) of the patient, expectedly corresponding to the target site for adjustment in the skeleton of the patient, so as to remove a skin slack, thereby determining the target site for adjustment. The finger may be any of the thumb, index finger, middle finger, third finger and fourth finger. The finger may be from either of the right and left hands. The palpation can be carried out in the same manner as in the palpation in the conventional methods for performing a chiropractic treatment. For details of the palpation in the conventional methods for performing a chiropractic treatment, reference can be made to, for example, the above-mentioned Non-Patent Documents 1 to 3.

Next, a preload is applied to the body surface of the patient by a method in which a forward end portion of the chiropractic apparatus is rather strongly pressed onto the body surface of the patient in the depthwise direction of the body of the patient. The preload can be carried out in the same manner as in the preload in the conventional methods for performing a chiropractic treatment. As mentioned above, the item (b) of each of FIGS. 1 to 11 shows a state where a preload is applied to the body surface of the patient.

Subsequently, the trigger member of the adjuster means is pulled to bring the adjuster means into action, thereby applying a thrust to the body surface of the patient. As mentioned above, the item (c) of each of FIGS. 1 to 11 shows a state where a thrust is applied to the body surface of the patient.

By performing the above-described operations, chiropractic treatment (adjustment) can be performed safely, effectively and efficiently, as compared to the case of the use of conventional chiropractic techniques.

With respect to the bone to be targeted in the chiropractic treatment using the apparatus of the present invention, there is no particular limitation, and any bones which are generally considered as candidate targets in chiropractic treatments can be subjected to the chiropractic treatment using the apparatus of the present invention. Examples of bones which can be targeted in the chiropractic treatment using the apparatus of the present invention include the occipital bone (OC), the cervical vertebrae (C1 to C7), the thoracic vertebrae (Th1 to Th12), the lumbar vertebrae (L1 to L5), the pelvis, and joints of limbs.

Any chiropractors having ordinary experience and skill can easily carry out a chiropractic treatment using the apparatus of the present invention. Further, even chiropractors having no experience of using any of the conventional chiropractic apparatuses (adjusters) can easily use the apparatus of the present invention.

INDUSTRIAL APPLICABILITY

By the use of the chiropractic apparatus of the present invention capable of forming a release surface, it becomes possible that, after a target site for chiropractic treatment (adjustment) is determined by performing a palpation on a patient, a satisfactory force of preload can be applied to the body surface of the patient through a relatively large contact area which is the total surface area of the forward end portion (thrust head) of the chiropractic adjuster means and, present therearound, the surface for forming a release surface. Therefore, by virtue of the relatively large contact area, there can be obtained advantages not only in that, during the preload, the patient's pain is small and the chiropractic adjuster means can be stably positioned on the body surface of the patient without causing damage to the body surface tissue, but also in that, after the preload, a satisfactory effect of treatment (adjustment) can be achieved even when using a small force of adjustment. Further, by virtue of the formation of a release surface around the thrust head of the chiropractic adjuster means when performing an adjustment, there can be achieved advantages not only in that the thrust head of the chiropractic adjuster means can be guided to a deep region (near to a target bone for adjustment) in the body of the patient, but also in that a thrust can be correctly applied to a small-area target site in the target bone. Thus, by the use of the chiropractic apparatus of the present invention, chiropractic treatment can be performed more safely, effectively and efficiently. Also, the chiropractic apparatus of the present invention is not only easily portable, but also enables even a chiropractor not having a high level skill to perform easily a safe, correct and effective adjustment of any bone of the entire body skeleton of the patient (such as the cranium, the spine, the lumbar vertebrae, the pelvis, and joints of limbs) without causing a pain to the patient. With respect to the bone to be targeted in the chiropractic treatment using the apparatus of the present invention, there is no particular limitation, and any bones which are generally considered as candidate targets in chiropractic treatments can be subjected to the chiropractic treatment using the apparatus of the present invention. Examples of bones which can be targeted in the chiropractic treatment using the apparatus of the present invention include the occipital bone (OC), the cervical vertebrae (C1 to C7), the thoracic vertebrae (Th1 to Th12), the lumbar vertebrae (L1 to L5), the pelvis, and joints of limbs.

I claim:

1. A chiropractic apparatus (1) comprising the following (i) and (ii):
   (i) a chiropractic adjuster (2) comprising:
      a thrust member (2F and 2B) extending in a longitudinal direction of said chiropractic adjuster (2) and having a thrust head (2B) constituting a forward end portion of said chiropractic adjuster (2),
      a driving member (2D and 2E) for applying a longitudinal forward thrust to said thrust member (2F and 2B), and
      a trigger member (2C) for operating said driving member (2D and 2E),
   (ii) a release-surface former (3) attached to said chiropractic adjusters (2), said release-surface former (3) having a preload surface (3A) for applying a preload to a body surface (P) of a patient and, when a longitudinal forward thrust is applied to said thrust member (2F and 2B) so as to give a thrust to the body surface (P) of the patient, the thrust head (2B) substantially protrudes beyond the preload surface (3A) in the longitudinal direction to thereby form a release surface (3B) around the thrust head (2B), the transverse surface area of the thrust head (2B) being smaller than the transverse surface area of the preload surface (3a).

2. The chiropractic apparatus (1) according to claim 1, wherein, when a longitudinal forward thrust is applied to said thrust member (2F and 2B) so as to give a thrust to the body surface (P) of the patient, an angle formed between said release surface (3B) and the longitudinal direction of said thrust member (2F and 2B) decreases as said thrust member (2F and 2B) moves forward in the longitudinal direction.

3. The chiropractic apparatus (1) according to claim 2, wherein said release-surface former (3) is comprised of a material capable of changing its shape, and wherein, when a longitudinal forward thrust is applied to said thrust member (2F and 2B) so as to give a thrust to the body surface (P) of the patient, said release-surface former (3) changes its shape as said thrust member (2F and 2B) moves forward in the longitudinal direction so that said release surface (3B) formed changes its shape accordingly, thereby resulting in the decrease in the angle formed between said release surface (3B) and the longitudinal direction of said thrust member (2F and 2B).

4. The chiropractic apparatus (1) according to claim 2, wherein said release-surface former (3) is comprised of at least one flap which is pivotably attached to the periphery of a forward end of said thrust head (2B), said flap being pivotable in the longitudinal direction of said thrust member (2F and 2B), wherein the angle formed between the preload surface (3A) of the flap for forming a release surface (3B) and the longitudinal direction of said thrust member (2F and 2B) is in the range of from 90 degrees to 20 degrees.

5. The chiropractic apparatus (1) according to claim 3, wherein said release-surface former (3) is comprised of a sheet made of a flexible material, wherein said sheet is attached to said chiropractic adjuster (2) so that said thrust head (2B) is covered by the sheet having its planar direction positioned perpendicular to the longitudinal direction of said thrust member (2F and 2B), and wherein, when a longitudinal forward thrust is applied to said thrust member (2F and 2B) toward the body surface (P) of the patient, said thrust head (2B) is caused to push forward said sheet, thereby forming said release surface (3B) and giving a thrust, through the sheet, to the body surface (P) of the patient.

6. The chiropractic apparatus (1) according to claim 3, wherein said release-surface former (3) is comprised of a rubber elasticity material body which is positioned so as to constitute a forward end portion of said thrust member (2F and 2B), wherein said forward end portion is exclusive of said thrust head (2B), wherein, when a longitudinal forward thrust is applied to said thrust member (2F and 2B) so as to give a thrust to the body surface (P) of the patient, said release-surface former (3) is compressed in the longitudinal direction of said thrust member (2F and 2B) to thereby protrude outwardly in a direction perpendicular to the longitudinal direction of said thrust member (2F and 2B), thereby forming said release surface (3B).

7. The chiropractic apparatus (1) according to claim 3, wherein said release-surface former (3) is comprised of a rubber elasticity material body which is attached to a side surface of said thrust head (2B), wherein, when a longitudinal forward thrust is applied to said thrust member (2F and 2B) so as to give a thrust to the body surface (P) of the patient, said release-surface former (3) is flexed, thereby forming said release surface (3B).

8. The chiropractic apparatus (1) according to claim 1, wherein said release-surface former (3) is positioned so as to surround said thrust head (2B) and has a forward end portion having a tapered shape.

9. A method for performing a chiropractic treatment, comprising using the chiropractic apparatus (1) of claim 1 so as to apply a thrust to a target site in a target bone of a patient.

10. A chiropractic apparatus (1) comprising the following (i) and (ii):

(i) a chiropractic adjuster (2) comprising:

a thrust member (2F and 2B) extending in a longitudinal direction of said chiropractic adjuster (2) and having a thrust head (2B) constituting a forward end portion of said chiropractic adjuster (2), a driving member (2D and 2E) for applying a longitudinal forward thrust to said thrust member (2F and 2B), and a trigger member (2C) for operating said driving member (2D and 2E), (ii) a release-surface former (3) attached along the periphery of a forward end of the thrust head (2B), said release-surface former (3) having a preload surface (3A) for applying a preload to a body surface (P) of a patient and, when a longitudinal forward thrust is applied to said thrust member (2F and 2B) so as to give a thrust to the body surface (P) of the patient, an angle formed between the release surface (3B) and the longitudinal direction of said thrust member decreases as the thrust member (2F and 2B) moves forward in the longitudinal direction.

* * * * *

UNITED STATES PATENT AND TRADEMARK OFFICE
CERTIFICATE OF CORRECTION

PATENT NO. : 8,709,041 B2
APPLICATION NO. : 13/818156
DATED : April 29, 2014
INVENTOR(S) : M. Harada Page 1 of 1

It is certified that error appears in the above-identified patent and that said Letters Patent is hereby corrected as shown below:

In the Claims

Column 20, line 67 (claim 1, line 14), please change "adjusters (2)," to -- adjuster (2), --

Signed and Sealed this
First Day of July, 2014

Michelle K. Lee
*Deputy Director of the United States Patent and Trademark Office*